United States Patent [19]

Klagsbrun

[11] Patent Number: 5,235,042

[45] Date of Patent: Aug. 10, 1993

[54] ENDOTHELIAL CELL GROWTH FACTOR

[75] Inventor: Michael Klagsbrun, Newton, Mass.

[73] Assignee: The Children's Medical Center Corporation, Boston, Mass.

[21] Appl. No.: 432,803

[22] Filed: Nov. 6, 1989

Related U.S. Application Data

[60] Division of Ser. No. 849,045, Apr. 7, 1986, Pat. No. 4,882,275, which is a continuation-in-part of Ser. No. 584,604, Feb. 29, 1984, abandoned.

[51] Int. Cl.$^5$ .................. C07R 13/00; C07K 15/06
[52] U.S. Cl. .................................................. 530/399
[58] Field of Search ................... 530/399; 514/14, 15, 514/21

[56] References Cited

U.S. PATENT DOCUMENTS

| | | | |
|---|---|---|---|
| 4,785,079 | 11/1988 | Gospodarowicz et al. | 530/399 |
| 4,902,782 | 2/1990 | Gospodarowicz et al. | 530/399 |
| 4,956,455 | 9/1990 | Esch et al. | 530/399 |
| 4,994,559 | 2/1991 | Moscatelli et al. | 530/399 |
| 5,026,839 | 6/1991 | Moscatelli et al. | 530/399 |

FOREIGN PATENT DOCUMENTS

WO87/01728 3/1987 PCT Int'l Appl.

OTHER PUBLICATIONS

Marx, J., "Holding the Line Against Heart Disease", Science, 248: 1491-1493, Jun. 1990.
Shing et al. (1985) *J. Cell Biochem* 29:275-287.
Maciag et al. (1982) *J. Biol. Chem.*
Thomas et al. (1984), Proc. Nat'l. Acad. Sci., USA 81, 357-361.
Klagsburn (1980) *J. Biolog. Chem.* 225:10859-10864.
LaBrecque et al. (1982) *Fed. Proc.* p. 620 Abstract #2051.
Heparin-Sepharose CL-6.
Shing et al. (1983) Abstracts, 74th Annual Meeting of Am. Soc. of Biol. Chemists, No. 418, p. 1829.
Shing et al. (1983) Abstracts, 23rd Annual Meeting of the Am. Soc. for Cell Biol. No. 1488, p. 395a.
Clemmons et al. (1983) *Proc. Nat'l Acad. Sci* 80 1641-1645.
Sullivan and Klagsbrun (1985) *J. Biolog. Chem.* 260(4):2399-2403.
D'Amore and Klagsbrun (1985) *J. Cell Biol.* 99:1545-1549.
Lobb et al. *J. Biol. Chem.* 261(4):1924 (1986).
Maciag et al. (1984) *Science* 225:932-934.
Conn and Hatcher (1984) *Biochem. and Biophys. Res. Comm.* 124(1):262-268.
Lobb and Fett (1984) *Biochem.* 23:295.
Gospodarowicz et al. (1985) *Biochem. and Biophys. Res. Comm.* 128(2):554-562.
Bohen et al. (1984) *Proc. Nat'l Acad. Sci.* 81:5364-5368.
Bohlen et al. (1985) *J. Cell Biochem* (Supp) 9a:133.
Esch et al. (1985) *Proc. Nat'l Acad. Sci.* 82:6507-6511.
Gimenez-Gallego et al. (1985) *Science* 230 (4732:1385-1389.

(List continued on next page.)

*Primary Examiner*—Lester L. Lee
*Attorney, Agent, or Firm*—Fish & Richardson

[57] ABSTRACT

Endothelial cell growth factor (ECG) from various sources possesses a strong and specific affinity for heparin. This strong affinity of ECG for heparin enables removal of undesired impurities from a mixture comprising ECG by: a) contacting immobilized heparin with the mixture to form a heparin-ECG complex; b) separating uncomplexed mixture from the complex; and c) contacting the complex with a salt solution of a salt concentration and pH effective to separate the ECG from the heparin. The resulting purified ECG (or fragment thereof) is useful in therapeutics and as an additive for cell culturing. The purified ECG is also useful to raise antibodies that are used in therapeutics and in ECG immunoassays.

13 Claims, 5 Drawing Sheets

OTHER PUBLICATIONS

Bohlen et al. *FEBS* 185 (1)177-181.
Burgess et al., *Ann. Rev. Biochem.* 575, 577 (1989).
Gospodarowicz, *Nature* 249:123 (1974).
Gospodarowicz, *J. Biol. Chem.* 250:2515 (1975).
Gospodarowicz, *J. Biol. Chem.* 253:3726 (1978).
Westall et al., *PNAS USA* 75:4675 (1978).
Gospodarowicz et al., *J. Biol. Chem.* 257:12266 (1982).
Shing et al., *Science* 223:1296 (1984) (Mar.).
Gospodarowicz et al., *PNAS USA* 81:6963 (1984) (Nov.).
Klagsbrun et al., *PNAS USA* 82:805-809 (1985).
Thomas *FASEB J.* 1:434 (1987).
Lobb, *Eur. J. Clin. Invest.* 18:321 (1988).
Gospodarowicz, *Crit. Rev. Oncog.* 1:1 (1989).
Lehninger, *Biochemistry* 2d. Ed. 162 (1977).
Lehninger, *Principles of Biochemistry* 144-145 (1982).
Connolly et al., *J. Clin. Invest.* 84:1470-1478 (1989).
Ferrara et al., *Biochem. Biophys. Res. Com.* 161:851-858 (1989).
Tischer et al., *Biochem. Biophys. Res. Com.* 165:1198-1206 (1989).

FIG. 1B 1 2
SLOT NUMBER

FIG. 3A 1 2
SLOT NUMBER

ENDOTHELIAL CELL GROWTH FACTOR

CROSS REFERENCE TO RELATED APPLICATION

This is a divisional application of applicant's earlier co-pending application (U.S. Ser. No. 06/849,045, filed Apr. 7, 1986, now U.S. Pat. No. 4,882,275), which in turn was a continuation-in-part of applicant's earlier co-pending application (U.S. Ser. No. 06/584,604, filed Feb. 29, 1984, now abandoned).

BACKGROUND

This invention relates to purification of protein factors, present in tissue in extremely minute quantities, that induce proliferation of endothelial cells, particularly capillary endothelial cells; it also relates to purified factor, antibodies to purified factor, and to methods of detecting and using the factor.

In normal tissue, endothelial mitogenic factors are implicated in a variety of physiological functions, including wound repair. Such factors are released by tumor cells and are also implicated in tumor angiogenesis, the growth of new blood vessels from surrounding tissue into the solid tumor, which supply nutrients necessary for the tumor's continued development.

Endothelial mitogenic factors have potential application in controlling angiogenesis, and thus controlling growth of tumors. Other potential applications include providing treatment for vascular disorders and vascularization of damaged or implanted tissue.

A crude endothelial cell growth factor preparation can be recovered from hypothalamus cells as disclosed in Maciag et al. (1982) *J. Biol. Chem.* 257(10) 5333–5336. The preparation includes ion exchange chromatography, but Maciag et al. do not report purification of ECG; for example, they do not report gels or silver staining of the preparation.

SUMMARY OF THE INVENTION

I have discovered that endothelial cell growth factor (ECG) possesses a strong add specific affinity for heparin, and this discovery enables various features described below. Because of this affinity, ECG's are also termed "heparin-binding" growth factors.

By endothelial cell growth factor, I mean a mammalian polypeptide or protein factor that stimulates proliferation of BALB/C 3T3 mouse cells and of capillary endothelial cells, and that is angiogenic as demonstrated by angiogenesis in chick chorioallantoic membrane. There are two classes of ECG, cationic endothelial cell growth factor (CECG) and anionic endothelial cell growth factor (AECG). In addition to 3T3 and capillary endothelial cell-growth stimulation, both classes of ECG share an extraordinary and specific affinity for heparin; the ECG-heparin bond is strong enough to require an eluting salt concentration significantly (at least 0.8M) higher than would be predicted on the basis of charge attraction between ECG and heparin.

Cationic endothelial cell growth factor is further characterized by:
a) molecular weight 18,000–20,000 daltons;
b) pI between 9.5 and 10.0;
c) elution from heparin at salt concentration of at least 1.3M NaCl (and most preferably 1.3–1.8M NaCl); and
d) immunoreactivity with certain immunospecific antibodies described below.

Anionic endothelial cell growth factor is further characterized by:
a) molecular weight 15,000–17,000 daltons;
b) pI between 4.8 and 5.2; and
c) elution from heparin at salt concentration of at least 0.85M NaCl(and most preferably 0.85–1.15M NaCl).

As detailed below, each class of ECG is present in a variety of cell-types. While there may be minor variations within each class from one cell-type to another, ECG shares sufficient structural similarity within each class, regardless of the source, to enable the purification and immunological processes described herein. ECG as used herein does not include substances that are sometimes termed growth factors but that do not stimulate growth of capillary endothelial cells.

The strong affinity of ECG for heparin enables removal of undesired impurities from a mixture comprising ECG by: a) contacting immobilized heparin with the mixture to form a heparin-ECG complex; b) separating uncomplexed mixture from the complex; and c) contacting the complex with a salt solution of a salt concentration and pH effective to separate the ECG from the heparin.

In preferred embodiments of the above method used to purify ECG, the mixture to be purified is obtained from ECG-associated cells and ECG-associated tissue. For example, ECG-associated tissue can be digested (e.g. with collagenase) to yield a crude extracellular matrix mixture. ECG-associated cells and tissue can be extracted to yield the mixture to be purified. The resulting mixture may be subjected to ion-exchange chromatography, and the ion exchange eluate is subjected to the above described heparin chromatography. To further purify the ECG solution eluted from the heparin, the contacting, separating, and eluting cycle is repeated at least once by contacting immobilized heparin with eluate from the previous cycle, separating the non-complexed eluate, and eluting ECG from immobilized heparin. The cycle is performed a sufficient number to times to yield ECG solution that is substantially purified. "Substantially purified" means substantially free from compounds normally associated with the factor in its natural state (e.g. proteins, carboyhydrates, lipids), and exhibiting constant and reproducible molecular weight, chromatographic response and elution profiles, amino acid composition and sequence, blocked or unblocked N-terminus, and biological activity. The term "substantially purified" is not meant to exclude artificial or synthetic mixtures of the factor with other compounds. The term is also not meant to exclude the presence of impurities which do not interfere with the biological activity of the factor, and which may be present, for example, due to incomplete purification. By the same token, the term is not meant to exclude compositions that are entirely free from detectable impurities.

Preferably, the substantially purified ECG is purified to one or more of the following standards: 1) substantially free from foreign protein detectable by silver staining (foreign protein being protein other than ECG, preferably active ECG); 2) less than 25 ng of foreign protein per gel; 3) specific cell-growth factor activity at least $10^4$ greater than the mixture originally applied to the immobilized heparin; or 4) specific growth factor activity of at least 1 unit (and most preferably at least 5 units) per ng of protein. A unit of growth factor activity is the amount of growth factor required to induce half-maximal incorporation of 3H-tymidine into 3T3 DNA; specific cell growth factor activity is units of cell growth activity per total weight of protein. Often the above purification levels are achieved in a single heparin elution, performed without other purification steps, or performed in combination with ion exchange chromatography. Multiple heparin chromatography steps achieve further purification. In one method of elution, the complex is contacted with a flowing salt solution, and the salt concentration of the solution is gradually varied. Fractions of eluant are collected and those enriched in ECG are recovered.

Exemplary mammalian tissue for producing ECG is hypothalamus, pituitary, cartilage, retina, bone, or brain tissue or tumor, most preferably chondrosarcoma tumor or hepatoma cell or tumor. Commercial preparations of tissue such as hypothalamus or pituitary may also be used as a source of crude ECG. Pituitary-derived ECG, cartilage-derived ECG, chondrosarcoma-derived ECG, and hepatoma-derived ECG are cationic. Brain, hypothalamus and bone tissue yield both a cationic and an anionic ECG. Retina-derived ECG is anionic.

In one particularly preferred embodiment: a) hepatoma cells are cultured and extracted; b) the extract is subjected to cation exchange chromatography; c) the cation exchange eluate containing ECG activity is contacted with immobilized heparin to form an ECG-heparin complex; d) the uncomplexed eluate is separated from the complex; e) the ECG is eluted from the immobilized heparin by contacting the complex with a salt solution of salt concentration and pH effective to separate said heparin from said ECG; f) the ECG-containing solution is recovered; and, optionally, g) the recovered solution is contacted with immobilized heparin, and separation and elution are performed. If necessary, step g) is repeated until the recovered ECG-containing solution is substantially pure, e.g. it has substantially no protein detectable by silver stain, other than ECG, and the specific cell-growth factor activity is at least 1 unit (most preferably at least 5 units) per ng of total protein.

The unusually strong and specific heparin-ECG affinity enables preparation of substantially pure ECG. The purified ECG has a specific growth factor activity of at least 1 unit (and most preferably at least 5 units) per ng of protein. The purified ECG preferably is obtained by the above-described method of purification from ECG-producing cells.

CECG is characterized above and may be further characterized by immunoreactivity to antibodies raised to at least one of the following epitopes:

1) pro-ala-leu-pro-glu-asp-gly-gly-ser-gly-ala-phe-pro-pro-gly-;
2) arg-ile-his-pro-asp-gly-arg-val-asp-gly-val-; and
3) ala-ile-leu-phe-leu-pro-met-ser-ala-lys-.

Preferably a peptide containing one of the above epitopes is covalently bound, via a C-terminal cys residue, to a carrier. These fragments are portions of the bovine pituitary basic fibroblast growth factor (FGF) reported by Esch et al. *Proc. Nat'l. Acad. Sci.* USA 82:6507–6511 (1985). The first sequence above is also reported by Gospodarowicz et al. *Proc. Nat'l Acad Sci.* USA 81:6965–6967 (1984).

Most preferably the ECG described above is a factor derived from mammalian cells, e.g. rat chondrosarcoma tumor, in which case it is termed rat ChDGF, or human hepatoma cells in which case it is termed human HDGF. By "derived", I mean that the polypeptide at issue is actually purified from the ECG-associated cells or tissue, respectively; alternatively, it is produced by a cell genetically engineered to produce a polypeptide identical to ChDGF or HDGF produced by naturally occurring chondrosarcoma tumor or hepatoma cells, respectively.

The invention also features antibodies that are immunoreactive with ECG, the antibodies being raised to purified ECG as described above or to a fragment thereof, e.g. one of the above-described epitopes. The antibody can be used in a method of detecting ECG (e.g. ChDGF or HDGF) in a sample, by contacting the sample with the antibody and detecting formation of immunological complex between the antibody and ECG.

Finally, the invention features a pharmaceutically acceptable composition comprising a neutral carrier and the above-described purified ECG (e.g. ChDGF or HDGF), an antigenic fragment thereof, or an antibody as described above. The pharmaceutical composition is useful to evaluate the ability of ECG or a fragment thereof to generate an immune response affecting tumor angiogenesis, or the ability of anti-ECG antibodies to affect tumor angiogenesis.

In preferred embodiments of the ECG, the antibody, the method of detecting, and the pharmaceutical composition, the ECG is derived from mammalian (most preferably human) hepatoma cells.

Other features and advantages of the invention will be apparent from the following description of the preferred embodiment and from the claims.

DESCRIPTION OF THE PREFERRED EMBODIMENT

Figures

Source of Crude ECGF

ECG can be purified from various types of normal and tumor mammalian tissue or cells. Hypothalamus tissue is a readily available source of both cationic and anionic ECG. Tumor tissues yielding ECG include, by way of example, chondrosarcoma and hepatoma tissue. Normal mammal tissue also yield ECG, for example, hypothalamus cartilage, pituitary, retina, brain, and bone tissue. ECG-associated cells include hepatoma cells.

Tissue is digested with collagenase to produce an extracellular matrix and cellular fractions according to a method such as that described in Azizkhan et al. (1983) *Can. Res.* 43:3281-3286. The crude extracellular matrix serves as the ECG source. Also the tissue can be extracted with NaCl or guanadine hydrochloride to yield an extract. ECG-associated cells also can be extracted, e.g. they can be frozen and thawed and homogenized.

Alternatively, commercial preparations of hypothalamus which can be used as a crude source of ECG for the method of the invention include: "Endothelial Cell Mitogen", sold by Biomedical Technologies, Inc., Cambridge, Mass., "Endothelial Cell Growth Supplement" sold by Collaborative Research, Inc. of Waltham, Mass.; and "Fibroblast Growth Factor" also sold by Collaborative Research, Inc. These commercial preparations may be purified to yield ECG by applying them to columns in the same manner as is described herein for ECG derived from tumor and normal tissue.

As detailed below, particularly preferred sources of ECG are tumor lines, such as chondrosarcoma tumor or hepatoma cells (most preferably the latter), such as the cells listed in Fogh et al., *J. Nat'l. Cancer Inst.* 59:221-225 (1977); Human Tumor Cell Bank, Sloan-Kettering Institute, New York, N.Y.

Immobilized Heparin

Heparin is a sulfated glycosaminoglycan (GAG). It is negatively charged, and may be readily immobilized by various techniques. One system for immobilizing heparin is a sepharose substrate in a commercially available heparin/sepharose column, such as columns sold by Pharmacia, Inc of Piscataway, N.J. Any other inert substrate is suitable for immobilizing heparin, including, by way of example only, agarose.

Heparin from any commercial source may be used. For example, heparin from Hepar, Inc. or from Canada Packers, Ltd. of Toronto, Canada may be linked to sepharose using the cyanogen bromide technique described by Iverius (1971) *Biochem. J.* 124:677-683. Ogamo et al. (1982) *Carbohydrate Research* 105:69-85 describes a method of coupling macromolecules related to heparin with substrates using 1 ethyl-3(3-dimethylaminopropyl) carbodiimide hydrochloride (EDAC) as a coupling agent, which can be adapted to heparin-gel systems.

Elution

The extraordinary affinity of heparin for ECG permits dramatic purification by relatively simple and inexpensive elution techniques. Broadly, the crude heparin solution is applied to immobilized heparin to form a complex; the remainder of the solution is removed; the complex is washed in a buffer; and the heparin is eluted in a relatively strong salt solution.

The ECG will elute from the heparin when the salt solution strength overcomes the heparin-ECG bond. The strength of the heparin-ECG bond is such that the eluting salt solution is about 0.8M or more stronger than would be predicted on the basis of comparable similarly charged growth factors which lack specific heparin affinity. For example, anionic factors such as epidermal-derived growth factor do not bind at all to negatively charged heparin, but anionic ECG elutes at NaCl concentrations over 0.85M NaCl (preferably 0.85-1.15M NaCl). Non-ECG cationic factors such as platelet-derived growth factor elute at about 0.5M NaCl, but cationic ECG elutes at 1.3-1.8M NaCl.

Thus ECG-heparin affinity is not primarily a charge-related, chemical effect, but instead is a conformational biological interaction related to a complementary fit, such as the fit between antibodies and antigens. This fact enables a far better separation of ECG from related proteins than would be the case if ECG's affinity to heparin were such that it eluted at salt concentrations close to those of the related proteins.

While not being bound by any particular theory, the affinity of ECG for heparin appears to be related to ECG's cell-growth promoting function, in that heparin sulfate, the major GAG species on the endothelial cell surface, is structurally, and at high concentrations, biologically similar to heparin. Thus, these heparin-like cell-surface substances may bind specifically to growth factors which have affinity for heparin and are purified by the method herein. Other GAG species such as chondroitin sulfate or keratan sulfate do not exhibit a strong affinity for ECG.

The eluting solution is preferably NaCl, but numerous other compatible salt solutions such as KCl, ammonium bicarbonate, ammonium acetate, or various buffers may be used to provide the ionic strength to elute ECG. The pH of the solution should be close to neutral, preferably 6.8-7.2.

Preferably, elution is achieved by gradually increasing the salt concentration of a solution flowing over the immobilized heparin column, and collecting fractions which are assayed for ECG activity.

The purification may be achieved in one of several ways. First, the crude ECG solution may be purified in one step on a heparin column, with no supplementary purification, to yield a product with at least $10^4$ (and preferably $5 \times 10^4$ or more) greater activity than the crude solution. The solution may be recycled through the heparin column or subjected to additional heparin column purifications yielding greater purity. Preferably, after three cycles, ECG is purified to homogeneity being the only protein present that can be detected by silver staining, for example, using the method of Oakley et al. (1980) *Anal. Biochem.* 105:361 et seq.

Alternatively, the crude ECG solution may be subjected to purification on an appropriate ion exchange column before the heparin purification. For an anionic ECG, a suitable ion exchange column is DEAE Sephadex; for cationic ECG, a suitable ion exchange column is BioRex 70.

The ECGF Product

Characteristics of the two classes of ECG's are generally given above. Those characteristics of purified cationic ECG apply to ChDGF and HDGF in particular, and they include immunoreactivity with antigenic ECG fragments such as the 15-terminal amino acids of FGF, and specific growth factor activity at least 1 unit/ng.

ECG's stimulate proliferation of endothelial cells, for example, at a concentration of about 1 ng/ml. ECG's are angiogenic, as demonstrated by application of chondrosarcoma-derived growth factor to the chorioallantoic membrane. About 600 units of growth factor activity (120 ng) are required to induce strong angiogenesis within 24 hours on the 9-day chick chorioallantoic membrane. Histological sections reveal that neovascularization takes place in the absence of inflammatory cells. Angiogenesis may also be demonstrated by cornea vascularization. Shing et al. *J. Cell Bioch.* 29:275-287 (1985).

Anti-ECG

ECG, or fragments thereof, can be used to raise antibodies that are immunoreactive with ECG from various sources, for example, the above-described FGF fragments are antigenic and produce antibodies that bind to ECG. More specifically, substantially purified hepatoma-derived growth factor can be used to stimulate the production of antibodies. In addition, peptide fragments of the substantially purified HDGF which are both immunogenic and immunospecific can also be used to raise antibodies.

To produce antibodies, the HDGF or peptide fragment may be coupled to a carrier protein such as albumin or keyhole limpet hemocyanin (KLH), utilizing techniques well known and commonly used in the art. Additionally, the HDGF or peptide fragment can be mixed with an immunologically inert or active carrier. Carriers which promote or induce immune responses, such as Freud's complete adjuvant, can be utilized. The antigenic material (HDGF or peptide fragment-carrier protein conjugate) is introduced into the immune system of the animal in which antibodies are to be raised. Both polyclonal antibodies and monoclonal antibodies, produced by well-known techniques, raised in response to the HDGF or immunogenic peptide sequences of the HDGF can be utilized in various ways.

These antibodies may be utilized in immunoassays to identify and quantitate the hepatoma-derived growth factor. The immunoassays within the scope of the present invention include both the sandwich technique and the competitive assay of enzyme-linked immunosorbent assay (ELISA). These assays are well known in that art and are described, for example, in Voller, A. et al., *The Enzyme Linked Immunosorbent Assay ELISA*), (Dynatech Europe 1979). As will also be understood by those of skill in the art, use of these immunodiagnostic assays involves antibodies raised in response to the HDGF or an immunogenic peptide fragment of HDGF. The assays also involve detectably labeling the peptide fragments and antibodies. Techniques for producing antibodies and detectably labeling peptide fragments and antibodies are well known in the art and will be known by one of skill in the art.

In addition, the materials for use in the assays of the invention are ideally suited for preparation of a kit. Such a kit may comprise a carrier means being compartmentalized to receive in close confinement one or more container means such as vials, test tubes, and the like. Each of said container means comprises one of the separate elements to be used in the method.

For example, one of said container means may comprise an antibody against HDGF as described above. Such fragments may be bound to a separate solid phase immunoabsorbent or directly to the inner walls of a container. A second container may comprise detectably labeled anti-antibody in lyophilized form or in solution.

The carrier may also contain, in addition, a plurality of containers each of which comprises different, predetermined known amounts of antibody. These latter containers can then be used to prepare a standard curve from which can be interpolated the results obtained from the sample containing the unknown amount of HDGF.

These antibodies may also be utilized to treat a patient suffering from angiogenesis of liver tumor cancer cells (hepatoma), by administering a therapeutically effective amount of the polyclonal antibodies, or preferably the monoclonal antibodies, to the patient.

Other Uses

The HDGF or angiogenic fragments thereof can be utilized to treat patients with damaged tissue or implanted tissue. These types of tissue will typically be in need of vascularization to aid in healing. Thus, the HDGF or fragments thereof can be administered to aid in the growth of new blood supply. Typically, the HDGF or fragments thereof will be administered in a pharmaceutical composition comprising a neutral or inert carrier and the HDGF or fragments of HDGF.

The purified ECG (e.g. ChDGF or HDGF) is also useful for culturing endothelial cells, and for stimulating tissue growth in vivo. The latter function can be achieved using polymeric delivery systems or implants such as those described in Folkman et al. U.S. Pat. No. 4,164,560, which is hereby incorporated by reference. The ability to purify ECG to homogeneity is particularly useful in enabling the generation of antibodies to ECG, e.g. using monoclonal techniques, which can be used for diagnostic assays for presences of ECG in bodily fluids.

The following examples of the invention are provided to illustrate the invention and not by way of limitation.

EXAMPLE 1

Purification of Chondrosarcoma-Derived ECG by Two Heparin Purification Cycles

Figure 1A:
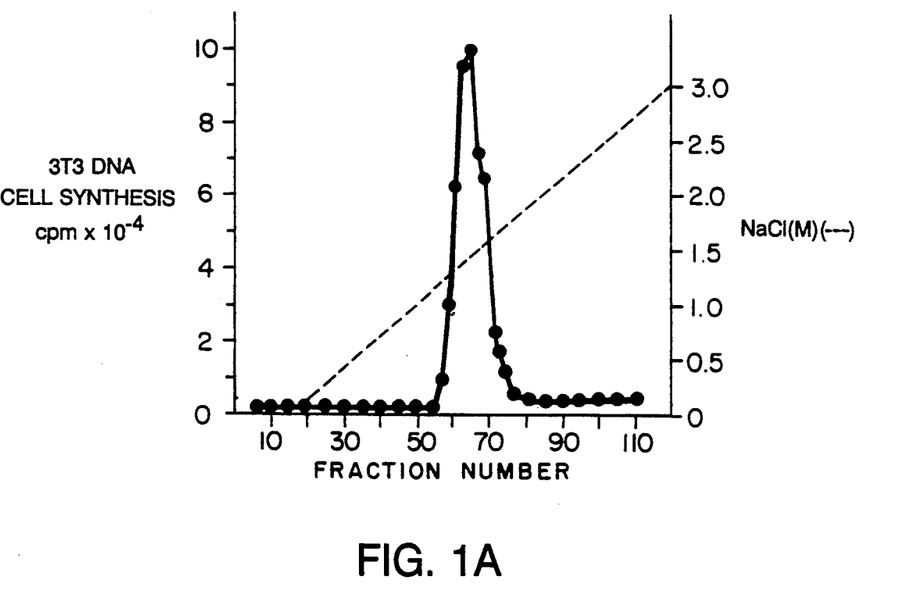
FIG. 1A is a graph demonstrating elution of chondrosarcoma-derived ECG from a heparin-sepharose column.
Figure 1B:
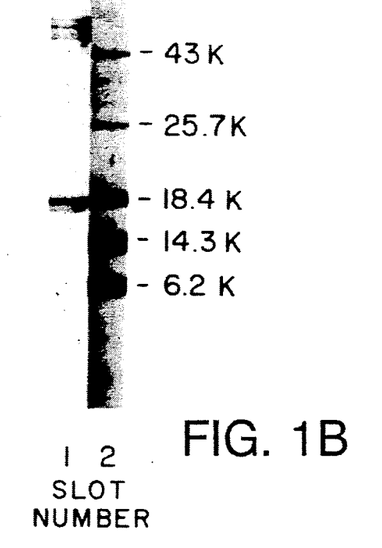
FIG. 1B shows the results of an SDS PAGE Electrophoresis of the ECG solution depicted in FIG. 1A.

A very highly purified preparation can be obtained from crude chondrosarcoma ECM by 2 cycles of heparin affinity chromatography, the first of which is shown in FIG. 1A. The elution profile of the second heparin-sepharose column is exactly the same as that for the first cycle shown in FIG. 1A. Analysis by sodium dodecyl sulfate polyacrylamide gel electrophoresis and silver stain of the peak of growth factor activity obtained after the second cycle on heparin-sepharose is shown in FIG. 1B (slot 1). Very few polypeptide bands are detectable. ECG shows as a prominent band with a molecular weight of about 18,000 as the major polypeptide species observed on the polyacrylamide gel.

Specifically, FIGS. 1A and 1B show the results of the following purification. Transplantable swarm rat chondrosarcoma was digested with collagenase to produce extracellular matrix (ECM) and cellular fractions. Crude ECM was used as the source of chondrosarcoma derived growth factors. Growth factor activity was tested by measuring $^3$H-thymidine incorporation into the DNA of quiescent monolayers of BALB/C 3T3 cells. One unit of activity is defined as the amount of growth factor required to induce half-maximal incorporation of 3H-thymidine into 3T3 DNA. Growth factor activity can also be demonstrated by stimulation of proliferation of endothelial cells as shown in connection with FIG. 2B in Example 2, below.

In FIG. 1A, chondrosarcoma ECM-derived growth factor (1000 units) dissolved in 20 ml water was applied to a column (1×8 cm) of heparin-sepharose (Pharmacia), equilibrated with 0.1M NaCl and 0.01M tris-HCl, pH 7.0. After a wash with 20 ml of equilibration buffer, growth factor activity was eluted with a 300 ml gradient of 0.1M NaCl to 3.0M NaCl in tris buffer at a flow rate of 30 ml/hour.

FIG. 1B shows sodium dodecyl sulfate polyacrylamide gel electrophoresis (SDS PAGE). Slot 1: chondrosarcoma ECM (500 mg, 6000 units) was applied to a heparin-sepharose column and the peak of growth factor activity (see FIG. 1A) was applied to a second heparin-sepharose column. This growth factor peak (250 ng, 1000 units) was analyzed by SDS PAGE using silver strain. Slot 2: molecular weight markers (Bethesda Research Laboratories).

EXAMPLE 2

Two-Step Purification

Figure 2A:
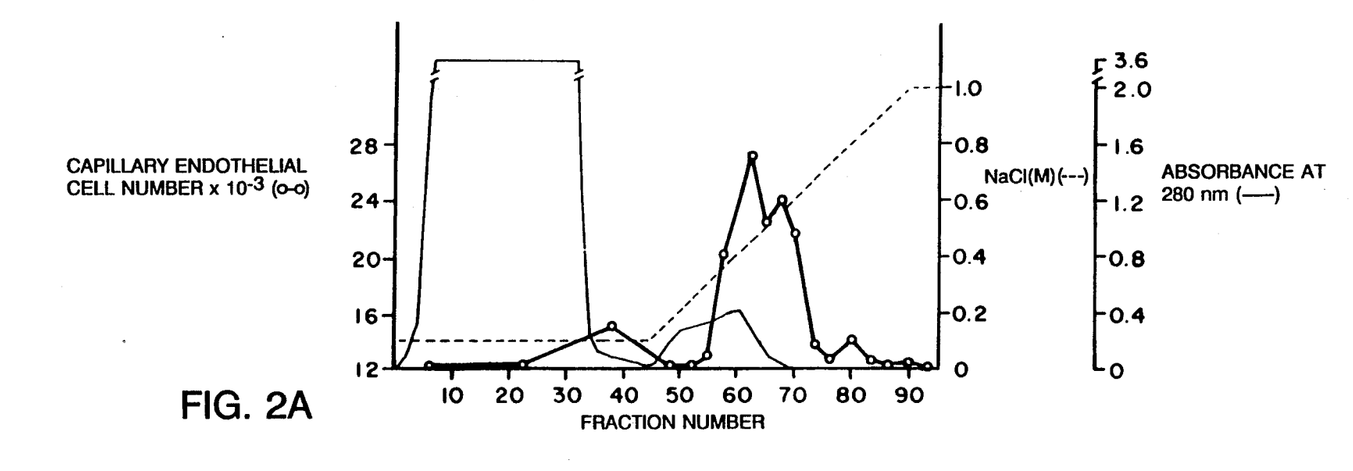
FIG. 2A is a graph demonstrating the first step in a two-step purification of chondrosarcoma-derived ECG.
Figure 2B:
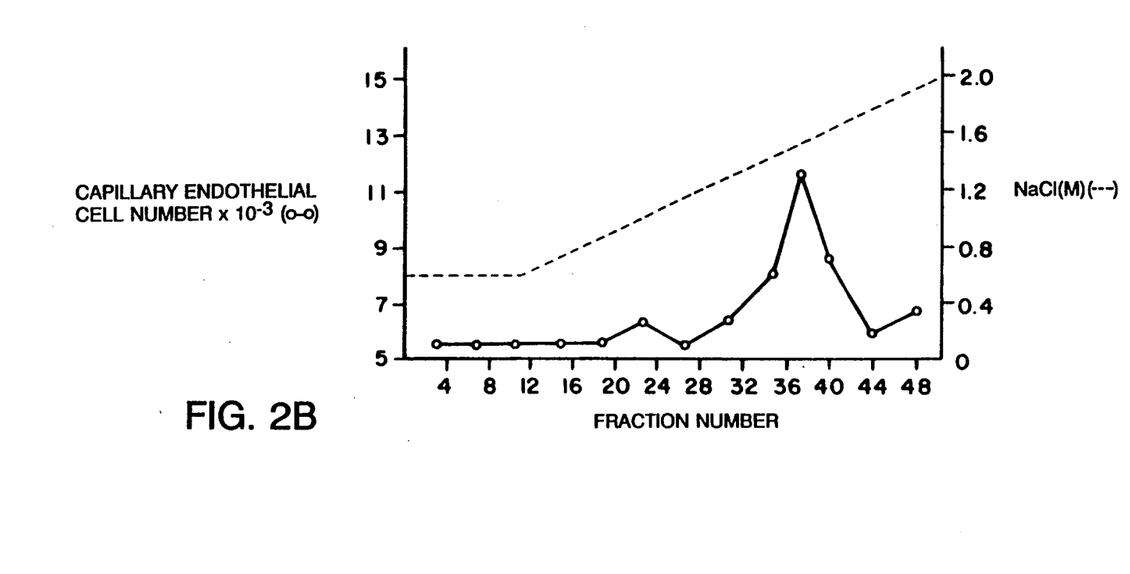
FIG. 2B is a graph demonstrating elution from a heparin column of the partially purified substance depicted in FIG. 2A.

FIG. 2 shows a two-step purification of chondrosarcoma-derived growth factor. To measure endothelial cell-growth activity, bovine capillary endothelial (BCE) cells were grown as described by Folkman et al. (1979) *Proc. Nat. Acad. Sci.* USA 76:5217. The cells (passage 4 to 14) were resuspended in Dulbecco's modified Eagle's medium supplemented with 10% calf serum (DMEM-CS) and plated sparsely into 24-well plates, (16 mm diameter, Costar) at a concentration of 10,000 cells/0.5 ml/well. On the following day, unattached cells were removed and attached cells (approximately 50% plating efficiency) were incubated with DMEM-CS in the absence or presence of growth factor. After 72 hours of incubation at 37°, the cells were detached with 0.25% trypsin and counted in a Coulter particle counter.

FIG. 2A shows BioRex 70 cation exchange chromatography. Crude chondrosarcoma ECM (1.35 grams/75 ml, 10,000 units prepared from 6 tumors of about 3 cm in diameter each) was analyzed on a 2.5×30 cm BioRex 70 column (2.5×20 cm, 200–400 mesh, Biorad), equilibrated with 0.1M NaCl and 0.01M tris-HCl, pH 7.0. After a wash with 50 ml of equilibration buffer, all of the growth-factor activity, but less than 0.01% of the protein in the crude mixture, adheres to the column. Growth factor activity was eluted with a 300 ml gradient of 0.1M NaCl to 1.0M NaCl at a flow rate of 30 ml/hour.

FIG. 2B shows heparin-sepharose chromatography. The growth factor activity peak in FIG. 2A (3000 units) was analyzed on a 1×15 cm column equilibrated with 0.6M NaCl, 0.01M tris-HCl, pH 7.0. After a wash with 50 ml of equilibration buffer, the column was eluted with a 300 ml gradient of 0.6M to 2.0M NaCl in tris buffer at a flow rate of 30 ml/hour.

Figure 3A:
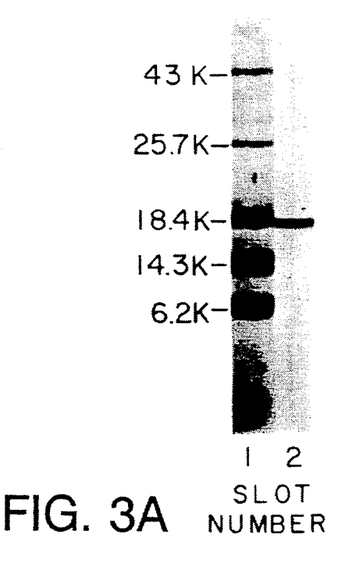
FIG. 3A demonstrates the SDS PAGE characterization of ECG purified in accordance with FIG. 2B.

All of the growth factor activity adheres to the column and elutes at 1.5M NaCl. Only 1 polypeptide band is observed after SDS PAGE and silver stain analysis of this growth factor activity peak (FIG. 3A, slot 2). The molecular weight of the polypeptide is about 18,000. This 18,000 molecular weight band is the same one previously shown in FIG. 1B (slot 1) to be the major polypeptide species purified by heparin-sepharose chromatography alone. When the single band preparation (FIG. 3A, slot 2) is analyzed by HPLC on TSK size exclusion columns, the growth factor activity elutes with a molecular weight of about 18,000 (FIG. 3B).

Figure 3B:
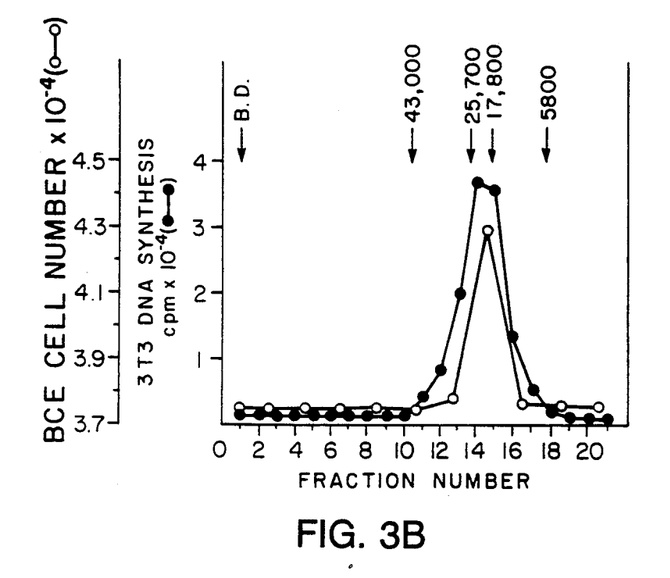
FIG. 3B demonstrates the size exclusion chromatographic characterization of the ECG purified in accordance with FIG. 2B.
Figure 3C:
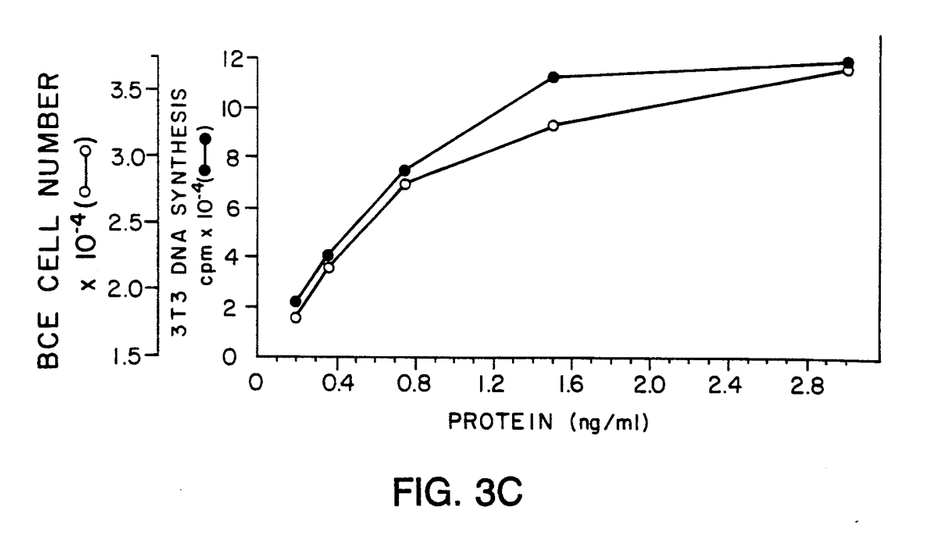
FIG. 3C demonstrates growth factor activity of the ECG purified in accordance with FIG. 2B.

FIG. 3 shows characterization of the purified chondrosarcoma-derived growth factor, as follows.

FIG. 3A—SDS PAGE. Slot 1: Molecular weight markers (BRL). Slot 2: The peak fraction of growth factor activity (200 ng, 1000 units) obtained when crude chondrosarcoma ECM was purified by BioRex 70 chromatography (FIG. 2A) followed by heparin-sepharose chromatography (FIG. 2B).

FIG. 3B: Size exclusion chromatography. About 5,000 units of single band preparation (FIG. 3A, slot 2) was analyzed by HPLC (Beckman model 332 gradient liquid chromatography system) at room temperature on a TSK 2000 column (60 cm×7.5 mm inner diameter, Altex), equilibrated with 0.6M NaCl and 0.02M Tris-HCl, pH 7.0). The flow rate was 0.5 ml/min. Fractions were tested for growth factor activity on BCE (o-o) and 3T3 (•-•) cells.

FIG. 3C: Dose response. Pure growth factor (FIG. 3A, slot 2) was added at various concentrations to cultures of BCE (o-o) and 3T3 (•-•) cells.

The growth factor stimulates both capillary endothelial cell proliferation and DNA synthesis in 3T3 cells in a dose-dependent manner (FIG. 3C). Half-maximal stimulation (1 unit of activity) is induced by growth factor concentrations of about 1 ng/ml. In the 2-step purification procedure, the recovery of activity is about 5% and the yield of pure growth factor is about 1 $\mu$g from 5 grams of crude chondrosarcoma ECM.

EXAMPLE 3

A crude ECG solution was derived from bovine hypothalamus using collagenase digestion followed by extraction of the crude extracellular matrix as described above in Example 1. Elution was performed by washing the heparin-ECG complex in buffered solution, and varying NaCl concentration in a gradient from 0.1M to 3.0M at 30 ml/hour. ECG elutes in two peaks one at about 0.85–1.15M NaCl and another at about 1.3–1.8M NaCl. The first peak shows a pI of about 4.8–5.2 and the second peak shows a pI of about 9–10.0. The m.w. of the peaks is about 15–20,000.

EXAMPLE 4

A crude ECG solution was derived from bovine retina using collagenase digestion followed by extraction of the crude extracellular matrix as described above in Example 1. Elution was performed as described in Example 3 and the ECG elutes at NaCl=0.8–1.1M. The pI=4.8–5.2 and m.w.=between 15,000 and 17,000.

EXAMPLES 5 AND 6

A crude ECG solution derived from both bovine and human cartilage was purified by applying 50 mg/25 ml water to a 6.6 ml heparin sepharose column, and washing the heparin-ECG complex. In both cases ECG was eluted in an NaCl (30 ml/hour) gradient 0.1M to 3.0M. ECG eluates at between 1.3 and 1.8M NaCl. The pI=9.5–10.0; mw=about 18,000–20,000.

EXAMPLE 7

Endothelial Cell Growth Supplement from Collaborative Research was purified by applying 50 mg/25 ml 0.1M NaCl and 0.01M tris-HCl to a 6.5 ml heparin sepharose column, and eluting with an NaCl solution at the above flow rate and concentration gradient. ECG elutes in two peaks similar to those described in Example 3, above.

EXAMPLE 8

Endothelial Mitogen from Biomedical Technologies, Inc. was purified by applying 150 mg/75 ml of the equilibration solvent described in Ex. 7, to a 6.5 ml column. ECG was eluted in an NaCl solution under the conditions of Example 3. ECG eluted in two peaks similar to those described in Example 3, above.

EXAMPLE 9

Pituitary-derived Fibroblast Growth Factor from Collaborative Research was purified by applying 10 micrograms/5 ml of the equilibration solvent described in Ex. 7, to a 6.5 ml column. ECG was eluted in an NaCl solution under the conditions of Example 3. ECG elutes at about 1.8M NaCl. The pI is about 9 and the m.w.=18,000 to 20,000.

EXAMPLE 10

Hepatoma - Derived Growth Factor (HDGF)

Figure 4:
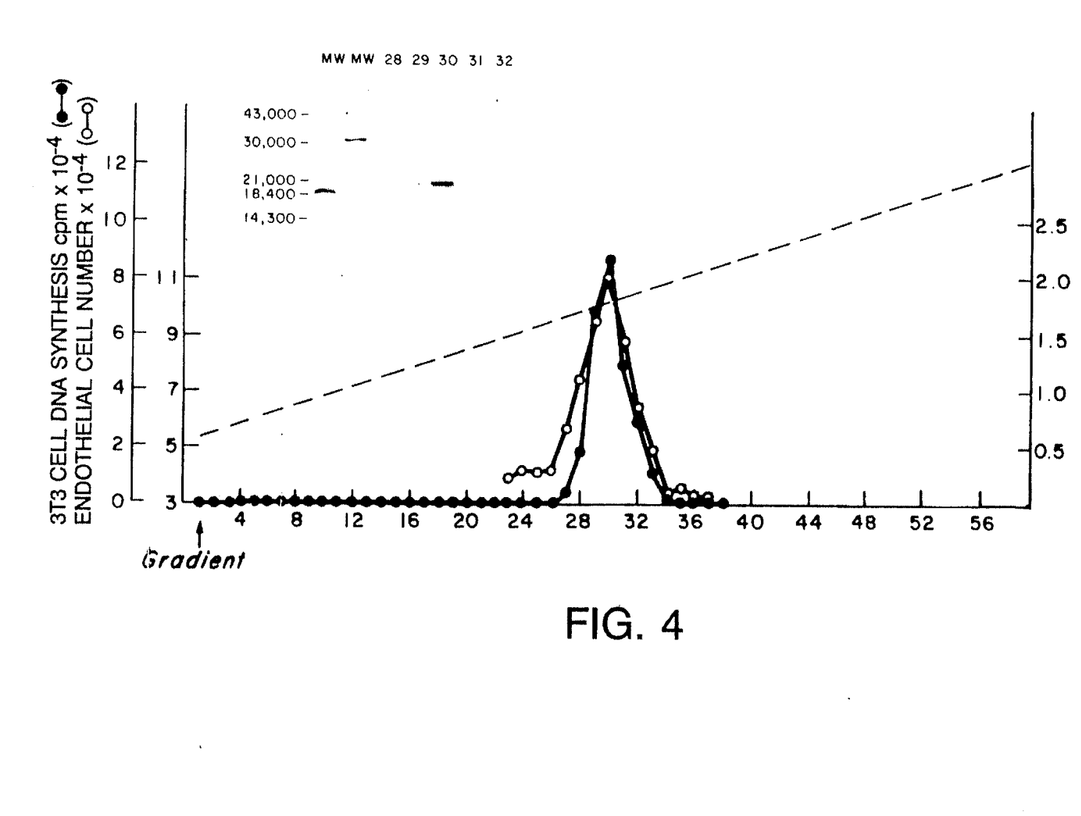
FIG. 4 is a graph demonstrating the cell-growth factor activity of various HDGF heparin elution fractions; the inset depicts the results of SDS PAGE and silver stain.
Figure 5:
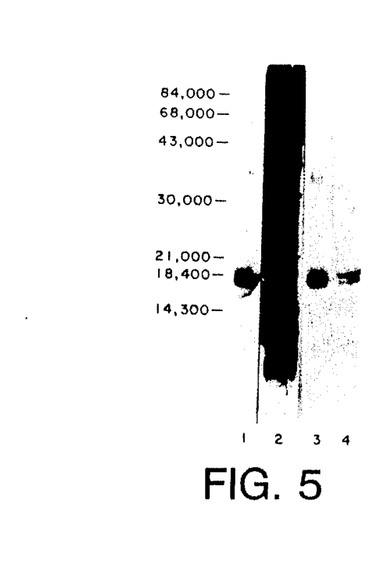
FIG. 5 is a protein or "Western" blot analysis of HDGF purified by BioRex and Heparin-Sepharose chromatography (Lanes 1 and 3) and purifed by BioRex 70 chromatography alone (Lanes 2 and 4). Lanes 1 and 2 were stained for protein; Lanes 3 and 4 were incubated with anti-FGF antiserum and visualized by antibody staining.

FIGS. 4-5 relate to the following specific example of purification of HDGF.

Human hepatoma cell line SK-HEP-1 (Fogh et al. cited above) was grown in suspension culture, and most of the growth factor activity was associated with the cells, so the cells were lysed by a succession of freezing, thawing, and homogenization.

HDGF was purified to homogeneity using a combination of BioRex 70 cation exchange and Heparin-Sepharose affinity chromatography, generally as described above. More specifically, SK-HEP-1 cells were grown in suspension as described in W. R. Tolbert et al., *Biotech. and Bioeng.*, 24:1671 (1982). About $5 \times 10^{10}$ cells were collected by centrifugation. The pellet, about 150 ml, was frozen, thawed and resuspended in 1500 ml of 1M NaCl, 0.01M Tris-HCl, pH 7.5. The hepatoma cells were disrupted by sonication or homogenization in a Waring Blender for 1 minute at room temperature. The homogenate was stirred overnight at 4 degrees C. and subsequently clarified by centrifugation at 25,000 g for 30 minutes The clarified supernatant was dialyzed against 0.015M NaCl, 0.01 Tris-HCl (pH 7.5) and mixed with 1750 ml of BioRex 70 (BioRad, 200-400 mesh), equilibrated with the same buffer, by stirring overnight a 4 degrees C. The BioRex 70 was collected, poured into a column (5×100 cm), washed with 2000 ml of equilibration buffer and then with 2000 ml of equilibration buffer and then with 2000 ml of 0.6M NaCl, 0.01M Tris-HCl, pH 7.5 at a flow rate of 60 ml/hour at 4 degrees C. Fractions were collected and monitored for the ability to stimulate DNA synthesis in BALB/c 3T3 cells and proliferation of capillary endothelial cells as previously described in M. Klagsbrun et al., *Proc. Nat. Acad. Sci. U.S.A.*, 225:10859-10866 (1980); and Klagsbrun et al. *Exp. Cell Res.* 105:99-108 (1977). Fractions containing HDGF were pooled (about 300 ml, 1.5 10$^6$ growth factor activity units and applied directly to a column fo Heparin-Sepharose (Pharmacia, 2×13 cm, 40 ml) equilibrated with 0.6M NaCl, 0.01M Tris-HCl, pH 7.5. After a wash of 200 ml with equilibration buffer, a 400 ml gradient of 0.6M NaCl, 0.01M Tris-HCl, pH 7.5 was applied to the column at a flow rate of 40 ml/hour at 4 degrees C. Fractions (7 ml) were collected and tested for conductivity and for the ability to stimulate DNA synthesis in 3T3 cells and proliferation of capillary endothelial cells.

In results depicted FIG. 4, the closed circles represent DNA synthesis, measured in counts per minute times $10^{-4}$, and the open circles representing capillary endothelial cell proliferation, measured as endothelial cell number times $10^{-4}$. The dotted line represents NaCl concentration gradient (right axis). Referring to FIG. 4, it may be seen that fractions 28-32 demomstrate the peak of HDGF biological activity.

The Insert of FIG. 4 shows the molecular weight of the fractions. About 10% of each of the active fractions (28-31) were dialyzed against distilled $H_2O$, lyophilized and analyzed by SDS-polyacrylamide gel electrophoresis (Laemmli, *Nature.*, 277: 680 (1970)) and silver stain (Oakley et al., *Anal. Biochem.*, 105:362 (1975)). The biologically active protein has a molecular weight of about 18,500.

One peak of growth factor activity, as measured by the ability of fractions to stimulate 3T3 cell DNA synthesis and capillary endothelial cell proliferation eluted at about 1.8M NaCl. Analysis of the active fractions by SDS-PAGE and silver stain revealed the presence of a single polypetide band with a molecular weight of about 18,500 (FIG. 4 Inset). The purified HDGF had a specific activity of about 5-7 units/ng and stimulated cell proliferation at about 0.5-1.0 ng/ml. A unit of growth factor activity was defined as the concentration of growth factor needed to stimulate half-maximal stimulation of DNA synthesis in 3T3 cells. After heparin purification, about $1-2 \times 10^4$ hepatoma cells were found to contain 1 unit of HDGF.

HDGF was desalted in preparation for sequence analysis by reverse phase chromatography on an HPLC C3 column, equilibrated at about pH2. At pH2, there is a complete loss of growth factor activity, and even if eluate from the column is immediately neutralized, the specific activity cannot be restored to within an order of magnitude of the starting material. Reverse phase HPLC thus irreversibly reduces specific activity below 1 unit/ng. Reverse phase HPLC showed two partially resolved peaks of biologically active HDGF eluting between 32 and 37% organics (acetonitrile and isoproponal: 50:50 (vol/vol), which confirms the finding discussed below regarding the "doublet" in the protein (or "Western") blot.

Specifically, HDGF purified by a combination of BioRex 70 and Heparin-Sepharose chromatography as described above was desalted by reverse phase high performance liquid chromatography (HPCL) using a Beckman model 334 HPLC gradient system. HDGF (abut 4,000,000 units, 80 ug, 60 ml) was applied to an RPLC C3 column (0.46×7.5 cm, Beckman Instruments) via a separate minipump (LDC/MiniRoy pump).

EXAMPLE 11

Comparision of HDGF to Fibroblast Growth Factor (FGF)

Hepatoma-derived growth factor was compared structurally, to fibroblast growth factor (FGF), a normal tissue endothelial cell growth factor described in Gospodarowicz et al., *Proc. Nat'l Acad. Sci.* USA, 81: 6963 (1984) and Esch et al., *Proc. Nat.'l Acad. Sci.* USA, 82:6507-6511 (1985). An antibody was raised to synthetic antigens comprising three bovine FGF sequences: a 16 amino acid amino terminal sequence of bovine FGF, (reported in Gospodarowicz et al. (1984):

1) pro-ala-leu-pro-glu-asp-gly-gly-ser-gly-ala-phe-pro-pro-gly-;
2) arg-ile-his-pro-asp-gly-arg-val-asp-gly-val-; and
3) ala-ile-leu-phe-leu-pro-met-ser-ala-lys-.

The above peptides can be synthesized by the solid-phase method of Merrifield (Merrifield, *J. Am. Chem. Soc.* 85:2149 (1963)) using an automated applied Biosystems 430 synthesizer. Preferably, the C-terminal cys is added to the peptide for co-valent linkage to a carrier. For example, to synthesize peptide 1), a peptide synthesizer, t-butoxycarbonyl (Boc)-gly, was coupled to hydroxymethyl-phenylacetoaminodomethyl (Pam)- polystyrene resin and peptide assembly was carried out using Boc-amino acids (Peninsula Laboratories) to produce 1 gram of Boc-pro-ala-leu-pro-glu-asp(OBzl)-gly-gly-ser-(OBzl)-gly-ala-phe-pro-pro-gly-OCH2-Pam-resin. The resin (0.97 g) was treated with 10 ml anhydrous hydrogen fluoride in the presence of 1.0 ml p-cresol and 1.0 g p-thiocresol for 1 hour at 0 degress C. and extracted with diethyl ether and 30% glacial acetic acid. The peptide was desalted on a Sephadex G-25 column (2.5×90 cm) equlibrated with 1M glacial acetic acid and fractionated on an HPLC Vydac C4 reverse phase column (0.46×25 cm) using a linear gradient of 0-60% acetonitrile in 0.1% TFA.

The synthetic FGF peptide was conjugated to keyhole limpet hemocyanin (KLH) using 1-ethyl-3-(3-dimethylaminopropyl) carbodimide. Rabbits were immunized by multisite intradermal injections of KLH-peptide conjugate (500 ug) emulsified with complete Freund's adjuvant followed 3 and 6 weeks later with subcutaneous injections of 200 ug of KLH- peptide conjugate emulsified in incomplete Freund's adjuvant. The titer of the antisera after the second booster injection was about 1:4000-1:9000 as determined in an ELISA-assay using unconjugated FGF peptide as the antigen.

The polyclonal antibodies that were produced to fragment 1) were tested for their ability to cross-react with HDGF (FIG. 5).

As shown in FIG. 5, the cross-reactivity of anti-FGF antisera for HDGF was analyzed by Western blot. Proteins were electrophoresed on an 18% SDS-polyacrylamide gel and transferred electrophoretically to BA-83 nitrocellulose paper (Trans-Blot cell, Bio-Rad). Portions of nitrocellulose paper were either stained for protein with "Aurodye colloidal gold reagent" (Janseen Life Sciences Products) or incubated with anti-FGF antiserum and visualized by successive incubations with biotinylated goat anti-rabbit antibodies, peroxidase-conjugated steptavidin and 4-chloro-1-napthol substrate. Replicate samples of HDGF purified by BioRex and Heparin-Sepharose chromatography were stained for protein (lane 1) and stained with antiserum to the FGF fragment (lane 3). Replicate samples of crude HDGF partially purified by BioRex 70 chromatography alone were stained for protein (lane 2) and stained for antibody (lane 4).

The antisera could be shown to be highly specific in its ability to detect HDGF in a crude mixture of protein. Of the many proteins found in the crude preparation of HDGF (lane 2), only a polypeptide doublet with molecular weights of about 18,000-19,000 was clearly immunoreactive with anti-FGF antiserum (lane 4). The nature of the doublet is unclear but suggests the presence of multiple forms of HDGF, which are "microheterogeneous" and of similar molecular weight. It is concluded that HDGF contains a sequence homologous to the above-described FGF sequence.

Sequencing performed on active fractions recovered from HPLC indicated that HDGF was blocked its N-terminus. Accordingly, HDGF was digested by drying, resuspending in buffer and digesting with trypsin (Cooper Biomedical). The tryptic fragments were applied to a reverse phase HPLC column (Vydac HPLC C6 columns, Separations Group 0.46×25 cm) and the fragments were separated with a 120 ml linear gradient of 0-60% acetonitrate in 0.1% TFA at a flow rate of 1 ml/minute. Peaks were collected, dried and resuspended for sequencing (Applied Biosystems 470A) as described in Hunkapillar et al., *Methods In Enzymology* 91:486 (1968).

One of the sequences was found to be: leu-pro-ala-leu-pro-glu-asp-gly-gly-X-gly-ala-phe-pro-pro-gly where X is an amino acid moiety that was not identified.

From this data it was concluded that the HDGF sequence shows homology with the FGF sequence. However, in HDGF, the sequence is internal, having at least two additional amino acids on its amino terminal side. Specifically, starting with its third amino acid residue (pro) the HDGF sequence corresponds to the amino terminal sequnece of bovine FGF. The HDGF sequence apparently shows the same homology with human FGF.

Other embodiments are within the following claims.

I claim:

1. Purified cationic endothelial cell growth factor (CECG) substantially free from other proteins detectable by silver staining, said CECG being characterized by a molecular weight as determined by SDS PAGE under non-reducing conditions of between 18,000 and 20,000 daltons, angiogenic activity, capillary endothelial cell proliferation, pI=9.5-10.0, and release from heparin at NaCl concentration of about 1.4M and higher.

2. The CECG of claim 1 characterized by a specific cell growth factor activity of at least 1 unit/ng.

3. The CECG of claim 1 characterized by a specific growth factor activity of at least 5 unit/ng.

4. The CECG of claim 2, obtained by a process comprising culturing ECG-producing cells to obtain a mixture comprising ECG, extracting said cells to yield a mixture, optionally subjecting said mixture to ionic exchange chromatography, contacting immobilized heparin with said mixture or said ionic exchange chromatography eluate to form a complex between said ECG and said heparin; separating uncomplexed mixture from said complex; and eluting said ECG from said immobilized heparin by contacting said complex with a salt solution of a salt concentration and pH effective to separate said ECG from said heparin.

5. The CECG of claim 2 further characterized in that said CECG is derived from chondrosarcoma tumor or hepatoma cells.

6. The CECG of claim 2 characterized in that said CECG exhibits immunoreactivity to antibodies raised to at least one of the following three epitopes:
   1) pro-ala-leu-pro-glu-asp-gly-gly-ser-gly-ala-phe-pro-pro-gly-;
   2) arg-ile-his-pro-asp-gly-arg-val-asp-val-asp-gly-val-; and
   3) ala-ile-leu-phe-leu-pro-met-ser-ala-lys-.

7. The CECG of claim 5 wherein said CECG is derived from hepatoma cells.

8. The CECG of claim 7 wherein said CECG is derived from human hepatoma cells.

9. The CECG of claim 4 wherein said CECG or AECG has a specific cell growth factor activity at least $10^4$ greater than the specific activity of said mixture.

10. A pharmaceutical composition comprising a neutral carrier and the CECG of claim 2 or an antigenic fragment thereof.

11. The composition of claim 10 wherein said composition comprises one of the following three peptide fragments:
1) pro-ala-leu-pro-glu-asp-gly-gly-ser-gly-ala-phe-pro-pro-gly;
2) arg-ile-his-pro-asp-gly-arg-val-asp-gly-val-; and
3) ala-ile-leu-phe-leu-pro-met-ser-ala-lys-.

12. The composition of claim 10 wherein said ECG is derived from hepatoma cells.

13. Purified cationic fibroblast growth factor (FGF) substantially free from other proteins detectable by silver staining and having a pI of about 9 and a molecular weight as determined by SDS PAGE under non-reducing conditions of between 18.000 and 20,000 daltons, said FGF characterized in that it elutes from heparin at NaCl concentration of about 1.8M.

* * * * *

UNITED STATES PATENT AND TRADEMARK OFFICE
CERTIFICATE OF CORRECTION

PATENT NO. : 5,235,042
DATED : August 10, 1993
INVENTOR(S) : Michael Klagsbrun

It is certified that error appears in the above-identified that said Letters Patent is hereby corrected as shown below:

In column 1, line 12, insert the following:

--This invention was made with government support under Grant No. CA 21763 awarded by the National Institutes of Health. The government has certain rights in the invention.--

Signed and Sealed this

Eighteenth Day of July, 1995

*Attest:*

BRUCE LEHMAN

*Attesting Officer*   *Commissioner of Patents and Trademarks*